(12) United States Patent
Rochon

(10) Patent No.: US 11,298,510 B2
(45) Date of Patent: Apr. 12, 2022

(54) ENDOVENOUS TREATMENT DEVICE WITH FLEXIBLE GUIDEWIRE ELEMENT

(71) Applicant: LSO MEDICAL, Loos (FR)

(72) Inventor: Philippe Rochon, Loos (FR)

(73) Assignee: LSO MEDICAL, Loos (FR)

( * ) Notice: Subject to any disclaimer, the term of this patent is extended or adjusted under 35 U.S.C. 154(b) by 244 days.

(21) Appl. No.: 16/465,718

(22) PCT Filed: Dec. 7, 2017

(86) PCT No.: PCT/EP2017/081833
§ 371 (c)(1),
(2) Date: May 31, 2019

(87) PCT Pub. No.: WO2018/104453
PCT Pub. Date: Jun. 14, 2018

(65) Prior Publication Data
US 2019/0290888 A1    Sep. 26, 2019

(30) Foreign Application Priority Data
Dec. 8, 2016 (FR) ...................................... 1662137

(51) Int. Cl.
*A61B 18/00* (2006.01)
*A61M 25/09* (2006.01)
(Continued)

(52) U.S. Cl.
CPC ....... *A61M 25/09041* (2013.01); *A61B 18/24* (2013.01); *A61B 18/245* (2013.01);
(Continued)

(58) Field of Classification Search
CPC ............................................ A61M 2025/0253
See application file for complete search history.

(56) References Cited

U.S. PATENT DOCUMENTS 5,409,483 A    4/1995  Campbell et al.
5,810,012 A *  9/1998  Lynch ............. A61M 25/09041
                                              600/434
(Continued)

FOREIGN PATENT DOCUMENTS

CN         1666719 A    9/2005
CN       101138483 A    3/2008
(Continued)

OTHER PUBLICATIONS

First Office Action issued in corresponding Chinese Patent Appln. No 201780075612.9, dated Jul. 30, 2021, with English translation.

*Primary Examiner* — Gary Jackson
*Assistant Examiner* — Anant A Gupta
(74) *Attorney, Agent, or Firm* — Blue Filament Law PLLC

(57) ABSTRACT

The endovenous treatment device has a delivery system (1; 2) for delivering of at least one treatment dose, which delivery system (1; 2) includes a wire element (1) for delivery of a treatment dose, which has a distal end part (10) able to be inserted, over at least part of its length, longitudinally into a vein, and which allows at least one treatment dose to be delivered into a vein in the region of the end of said distal end part (10). It additionally includes a drive system (4) by which the wire element (1) for dose delivery can be driven in at least a first given drive direction (R), and a guide (3) which is flexible along all or part of its length. The device includes a holding system (5) by which the distal end part (30) of the guide (3) can be temporarily held with respect to the body of a patient, near the insertion zone (7) of the wire element (1).

25 Claims, 14 Drawing Sheets

(51) Int. Cl.
*A61B 18/24* (2006.01)
*A61M 25/02* (2006.01)

(52) U.S. Cl.
CPC ............... *A61B 2018/0041* (2013.01); *A61B 2018/00196* (2013.01); *A61M 2025/0266* (2013.01); *A61M 2025/09125* (2013.01)

(56) References Cited

U.S. PATENT DOCUMENTS

| | | | |
|---|---|---|---|
| 6,152,948 | A | 11/2000 | Addis |
| 9,717,885 | B1 * | 8/2017 | Narciso Martinez . A61M 25/02 |
| 10,258,285 | B2 | 4/2019 | Hauck et al. |
| 2002/0072704 | A1 | 6/2002 | Mansouri-Ruiz |
| 2003/0191460 | A1 * | 10/2003 | Hobbs .................. A61B 18/245 606/15 |
| 2003/0236517 | A1 * | 12/2003 | Appling ................ A61B 18/24 606/7 |
| 2004/0044314 | A1 * | 3/2004 | Liska .................... A61M 25/02 604/180 |
| 2005/0203497 | A1 * | 9/2005 | Speeg .................... A61B 18/24 606/15 |
| 2007/0000498 | A1 * | 1/2007 | Glynn .................. A61B 8/4488 128/852 |
| 2008/0064920 | A1 | 3/2008 | Bakos et al. |
| 2014/0163515 | A1 * | 6/2014 | Hyman ................. A61M 25/02 604/500 |
| 2015/0250489 | A1 | 9/2015 | Kaisha |

FOREIGN PATENT DOCUMENTS

| | | |
|---|---|---|
| CN | 101557768 A | 10/2009 |
| EP | 938871 A2 | 9/1999 |
| FR | 2617038 A1 | 12/1988 |
| WO | 9915237 A1 | 4/1999 |

* cited by examiner

ENDOVENOUS TREATMENT DEVICE WITH FLEXIBLE GUIDEWIRE ELEMENT

TECHNICAL FIELD

The present invention relates to the field of endovenous treatment by delivery into the vein of a treatment dose by means of a flexible wired element. The treatment dose may, in a non-limiting and non-exhaustive manner, consist of a dose of energy, delivered for example in the form of electromagnetic radiation, by means of sound or ultrasonic waves, radio-frequency waves, or a dose of thermal energy delivered by radiation and/or contact, or a dose of a product allowing treatment of the vein. The flexible wired element may be hollow or solid, and may in particular, in a non-limiting and non-exhaustive manner, be an optical fiber, a wired, cable-type element or a flexible probe or a flexible cannula.

PRIOR ART

In the field of endovenous treatment, the treatment of a vein via delivery into the vein of treatment doses by means of a flexible wired element, which is inserted longitudinally into the vein, and whose retraction must be controlled during treatment, constitutes prior knowledge. More particularly, in the field of endovenous laser therapy, better known by the acronym EVLT, it is customary to treat a vein by means of an endovenous laser (for example occlusion of saphenous varices by endovenous laser), the flexible wired element of which is an optical fiber used to emit electromagnetic radiation into the vein. For other types of endovenous treatment, the flexible wired element may, in a non-limiting and non-exhaustive manner, also be a flexible cable or probe or a flexible cannula.

Examples of endovenous treatment apparatus are described, for instance, in the following publications: US 2005/0131400, US2008/0097224, US2008/0097408, U.S. Pat. No. 6,814,727.

Usually, the removal of the flexible wired element inserted into the vein, for example an optical fiber, can be controlled during treatment by the practitioner by means of a motorized retraction system to withdraw the proximal end portion (farthest from the patient's body) of the flexible wired element by controlling the retraction rate. Such retraction can be carried out continuously or step by step.

It is advantageous to be able to operate a wired element having a significant length, so as to easily be able to locate the motorized retraction system and the treatment dose-delivery system outside the sterile operating field, such as, for example, the laser source in the case of an endovenous laser. The distal end portion (closest to the body of the patient) of the wired element must be introduced into the vein, and the wired element must be flexible enough such that the distal end portion of the wired element in the vein may be raised to the level of the area to be treated, since the vein path may be more or less circuitous. As a result, remote retraction, exerted outside the sterile field, currently requires tension to be exerted upon the flexible wired element, in order to effectively transmit the traction exerted on the proximal end portion of the flexible wired element to the distal portion of the wired element. In conclusion, the existing solutions provide for tension to be exerted upon the wired element at a point between its insertion point and the retraction system.

This tensioning of the flexible wired element entails several drawbacks.

It generally increases the risk of accidental and uncontrolled retractions of the flexible wired element from the vein during the treatment procedure. In particular, the slightest movement of the patient or the slightest impact on the flexible wired element can detrimentally cause accidental and uncontrolled retractions of the flexible wired element. The weight of the wired element, especially in cases where its length, and/or where the weight of the introducer catheter used to introduce the flexible wired element into the vein is significant, can detrimentally result in inadvertent and uncontrolled retraction of the wired element during the treatment procedure.

The tensioning of the wired element also requires that the retraction system be positioned along the axis of insertion of the wired element into the vein, which presents an additional constraint for the practitioner.

Tensioning also reduces mobility around the operating theater bed, to avoid contact with the flexible wired element.

PURPOSE OF THE INVENTION

One purpose of the invention is to propose a new endovenous treatment device, of the type comprising a flexible wired element for the delivery of treatment doses, which endovenous treatment device overcomes the above drawbacks, and in particular enables an endovenous treatment to be performed without the flexible wired element being tensioned and reducing the risk of accidental removal of the flexible wired element from the vein.

SUMMARY OF THE INVENTION

This purpose is achieved by the endovenous treatment device as described in claim 1.

This endovenous treatment device comprises a delivery system of at least one treatment dose, which delivery system comprises a wired treatment dose delivery element, which is flexible, which has a distal end portion designed capable of being inserted, at least over part of its length, longitudinally into a vein, and which enables delivery into a vein of at least one treatment dose in the region of the end of said distal end portion. The endovenous treatment device further includes a drive system for driving of the wired treatment dose delivery element in at least a first given drive direction. Characteristically according to the invention, the endovenous treatment device further comprises a guide which is flexible over all or part of its length, which has a proximal end portion and a distal end portion, and which allows the wired treatment dose delivery element to be guided over a portion of its length, with a proximal end portion, and, at the opposite end, a distal end portion of the wired treatment dose delivery element, which are not guided by the guide, and a holding system that enables the distal end portion of the guide to be temporarily held relative to the body of a patient, near the insertion zone of the wired treatment dose delivery element, the wired treatment dose delivery element being slidable in the direction of its length relative to the guide, so as to allow longitudinal insertion into a vein of the distal end portion of a wired treatment dose delivery element over at least a portion of its length when the distal end portion of the guide is held relative to a patient's body by means of the holding system, and locking means, which allows axial locking of the proximal end portion of the guide, at least in the drive direction of the wired treatment dose delivery element.

In this text, the term "distal" defines the front portion of an element, and particularly the front portion of the guide or the front portion of the wired treatment dose delivery element, which is closest to the human or animal body when performing endovenous treatment. The term "proximal" defines the rear portion of an element, and particularly the rear portion of the guide or the rear portion of the wired treatment dose delivery element, which is furthest from the human or animal body when performing endovenous treatment.

More specifically, the device constituting the invention may include the following additional and optional features, taken in isolation, or in combination with each other:

The holding system includes a holding part which is designed to be applied to the body of a patient so as to temporarily hold the distal end portion (30) of the guide relative to the body of a patient, close to the insertion zone of the wired treatment dose delivery element.

The holding part has a lower face for application of the holding part in contact with the body of a patient, and the wired treatment dose delivery element is slidable along the direction of its length, being guided by the distal end portion of the guide along a guide axis (A) which does not intersect the underside of the holding part.

The lower face of the holding part forms a support surface, in which the wired treatment dose delivery element is slidable along the direction of its length, being guided by the proximal portion of the guide, along a guide axis (A) which does not intersect with this support surface.

The lower face of the holding part forms a support surface which is flat or substantially flat, or is capable of being deformed so as to form a support surface which is flat or substantially flat when it is applied to the body and the guide axis (A) is substantially parallel to this support surface of the holding part.

The guide axis (A) is inclined relative to the support surface of holding part at an angle ($\alpha$), which allows longitudinal insertion of the wired treatment dose delivery element into a vein, by sliding the wired treatment dose delivery element in the direction of its length, when the support surface is applied against the body.

the holding part has a lower face for applying the holding part in contact with the body of a patient, on which the lower face of the holding part forms a support surface which is flat or substantially flat, or is capable of being deformed so as to form a support surface which is flat or substantially flat when applied to a body, wherein the wired treatment dose delivery element is slidable in the direction of its length, being guided by the distal end portion of the guide along a guide axis (A), which passes through this support surface and which is inclined with respect to this support surface of an angle ($\alpha$) permitting longitudinal insertion of the wired treatment dose delivery element into a vein, by sliding of the wired treatment dose delivery element lengthwise, when the support surface is applied against the body.

Said angle ($\alpha$) is less than or equal to 60°, preferably less than or equal to 45°, and more preferably less than or equal to 30°.

The holding part is permanently attached or can be permanently or removably attached to the distal end portion of the guide.

The holding part has a tubular through passage in which is slid and is attached the distal end portion of the guide.

The device further comprises an introducer catheter which is designed to be temporarily assembled with the distal end portion of the guide.

The guide is designed such that once slid onto the wired treatment dose delivery element, there remains in the guide a portion of the wired treatment dose delivery element which is accessible and can be manipulated by an operator.

The holding system comprises attachment facilities which allow the distal end portion (30) of the guide as well as, if necessary, the holding part to be temporarily attached to the body of a patient, close to the insertion zone of the wired treatment dose delivery element.

The attachment facilities comprise an adhesive element or an adhesive layer capable of bonding to the skin.

The drive system is a retraction system that drives the treatment dose delivery wired element backward in a drive direction (R) for removal from a vein of the distal end portion of the wired treatment dose delivery element.

The locking means are designed to axially lock the proximal end portion of the guide also in the direction (F) opposite to the drive direction (R) of the wired treatment dose delivery element.

The wired treatment dose delivery element is an optical fiber.

The device includes a source of electromagnetic radiation that can be coupled to the optical fiber.

The locking means comprise a two-part connector, an attached part which is attached to the drive system, and a removable part which is attached to the proximal end portion of the guide and which is designed to interoperate with the attached part for locking of the proximal end of the guide.

The guide includes a flexible guide sheath.

The guide comprises several assembled guide elements, including at least one flexible guiding element, and more particularly a flexible guide sheath.

The invention also relates to a use of the abovementioned endovenous treatment device for treating a vein, and in particular for treating a vein by means of electromagnetic radiation.

The invention also relates to a method for endovenous treatment as defined in claim 23.

More particularly, but not necessarily, the wired treatment dose delivery element is an optical fiber, and the step (4) of the method comprises emitting electromagnetic radiation into the vein by means of the optical fiber.

BRIEF DESCRIPTION OF THE DRAWINGS

The features and advantages of the invention will become apparent from reading the detailed description below of several particular embodiments of the invention, which particular variants are described as non-limiting and non-exhaustive examples of the invention, and with reference to the accompanying drawings in which.

DETAILED DESCRIPTION

Figure 1:
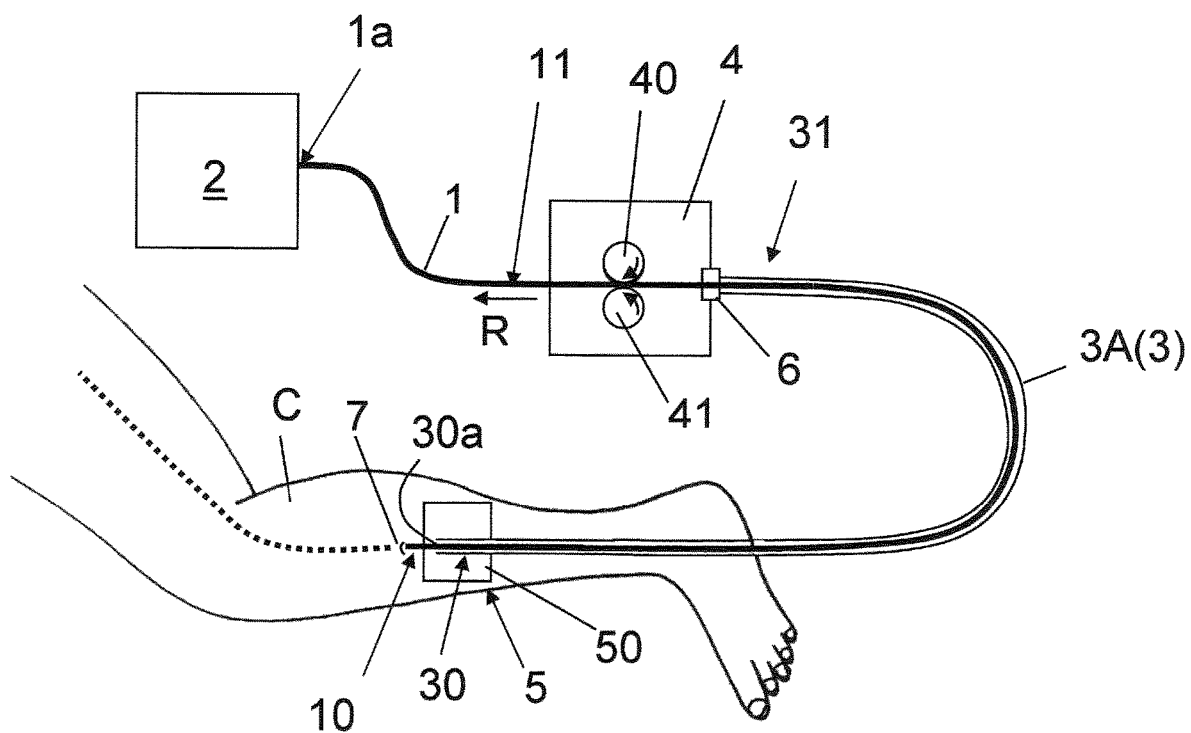
FIG. 1 is a schematic general view showing an example of an implementation of an endovenous treatment device relating to the invention, of the endovenous laser type, for laser treatment of a vein in the leg.

A schematic view of an endovenous treatment device with controlled retraction is shown in FIG. 1, comprising:
- a flexible wired element 1, which in this particular example is an optical fiber,
- a source of electromagnetic radiation 2, of the laser source type, which is coupled to a proximal end 1a of the optical fiber,
- a guide 3, which in this particular example is constituted of a flexible guide sheath 3A, which surrounds and guides the flexible optical fiber 1 over a portion of its length,
- a retraction system 4 which enables a pulling force to be exerted, in a controlled manner and towards the rear (direction R), upon the optical fiber 1, With reference to FIG. 1, the flexible guide sheath 3A has a proximal end portion 31 and, on the opposite side, a distal end portion 30, which ends with a distal opening 30a allowing the passage of the optical fiber 1. The optical fiber 1 is slid into the guide sheath 3A, so that the guide sheath 3A surrounds and guides the optical fiber 1 over a portion of its length, with a proximal end portion 11 of the optical fiber 1, and opposite a distal end portion 10 of the optical fiber 1 positioned outside the guide sheath 3A. The distal end of the optical fiber 1 which allows the emission of electromagnetic radiation into the vein is thus positioned outside the guide sheath 3A, and the practitioner can manually manipulate the distal end portion 11 of the optical fiber 1.

The length of the optical fiber must be sufficient so that its proximal end portion 31 can be positioned outside the sterile surgical field.

The sheath 3A allows sliding of the optical fiber 1 with preferably a minimum of friction and is preferably biocompatible.

The inner diameter of the sheath 3A must also be adjusted relative to the outer diameter of the optical fiber 1, in order to limit the radial movement of the optical fiber 1 in the sheath 3A and to allow efficient transfer of the longitudinal movements. If the difference between the inside diameter of the sheath 3A and the outer diameter of the optical fiber 1 is too great, it can cause a detrimental divergence between the moment when the motor of the retraction system 4 is activated and the moment of actual retraction of the fiber with respect to the sheath. By way of non-limiting and non-exhaustive examples, with an optical fiber 1 having an outside diameter of 900 μm, a sheath 3A having, for example, an internal diameter of 1000 μm, and with an optical fiber 1 having an outside diameter of 600 μm, a sheath 3A having for example an inner diameter of 700 μm is used.

Various materials can be used for the sheath 3A, including, in a non-limiting and non-exhaustive manner, the following materials: silicone, polyurethane, PTFE, PET, ETFE, latex, thermoplastic elastomer.

The retraction system 4 constitutes prior knowledge per se and comprises at least two rotary drive rollers 40, 41, between which the proximal end portion 11 of the optical fiber 1 is positioned. The roller 40 may be, for example, a motorized roller and the roller 41 may be, for example, a mounted roller which is free to rotate. These two rotary drive rollers 40, 41 make it possible to frictionally drive the optical sheath 1 to the rear (direction R) at a controlled speed which depends on the speed of rotation of the rollers 40, 41 during the controlled removal of the optical fiber from the vein to be treated.

The endovenous treatment device further comprises:
- a holding system 5 which, in this particular embodiment, enables the distal end portion 30 of the guide sheath 3A to be attached on the body C of a patient (in this case in FIG. 1 and in a non-limiting manner on the leg) near the insertion point 7 of the optical fiber in the body C,
- a locking system 6, which enables the proximal end portion 31 of the guide sheath 3A to be blocked axially with respect to the optical fiber 1, at least in the direction of retraction R of the optical fiber 1, in order to allow the relative rearward sliding of the optical fiber 1 relative to the guide sheath 3A.

Figure 2:
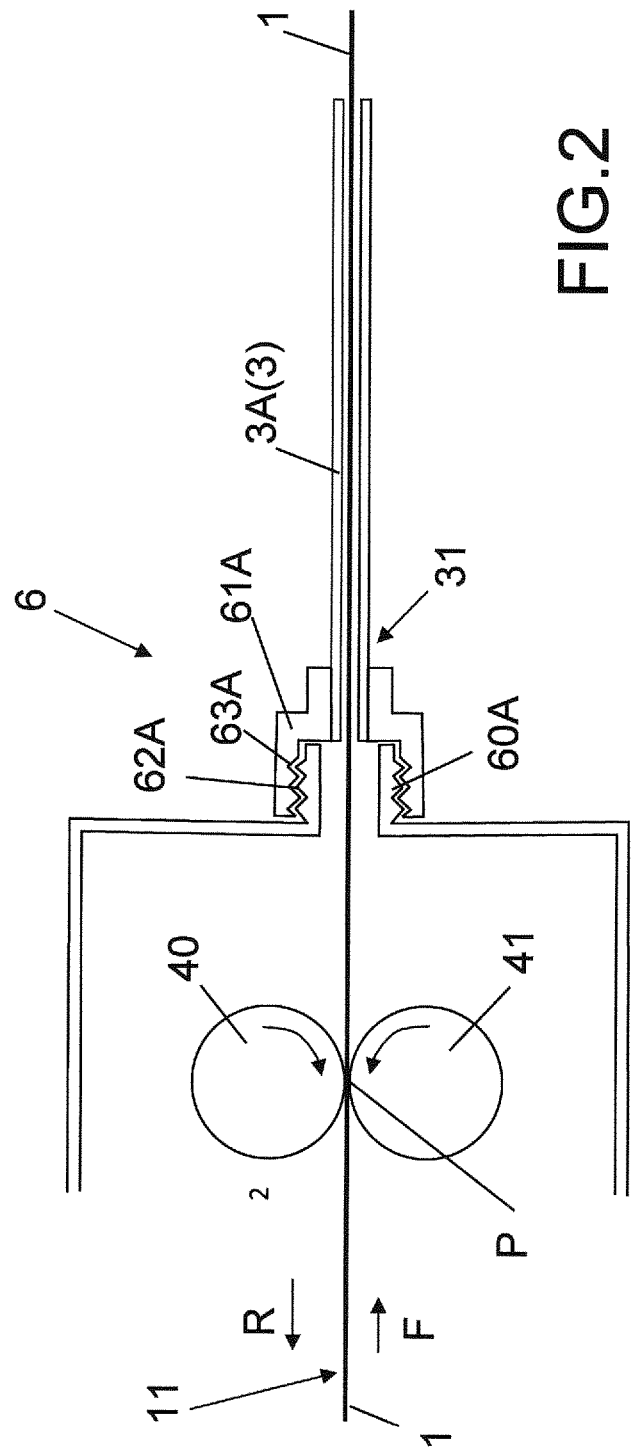
FIG. 2 is a cross-sectional view of a first embodiment of a connector for the proximal portion of the guide sheath of the endovenous treatment device.
Figure 3:
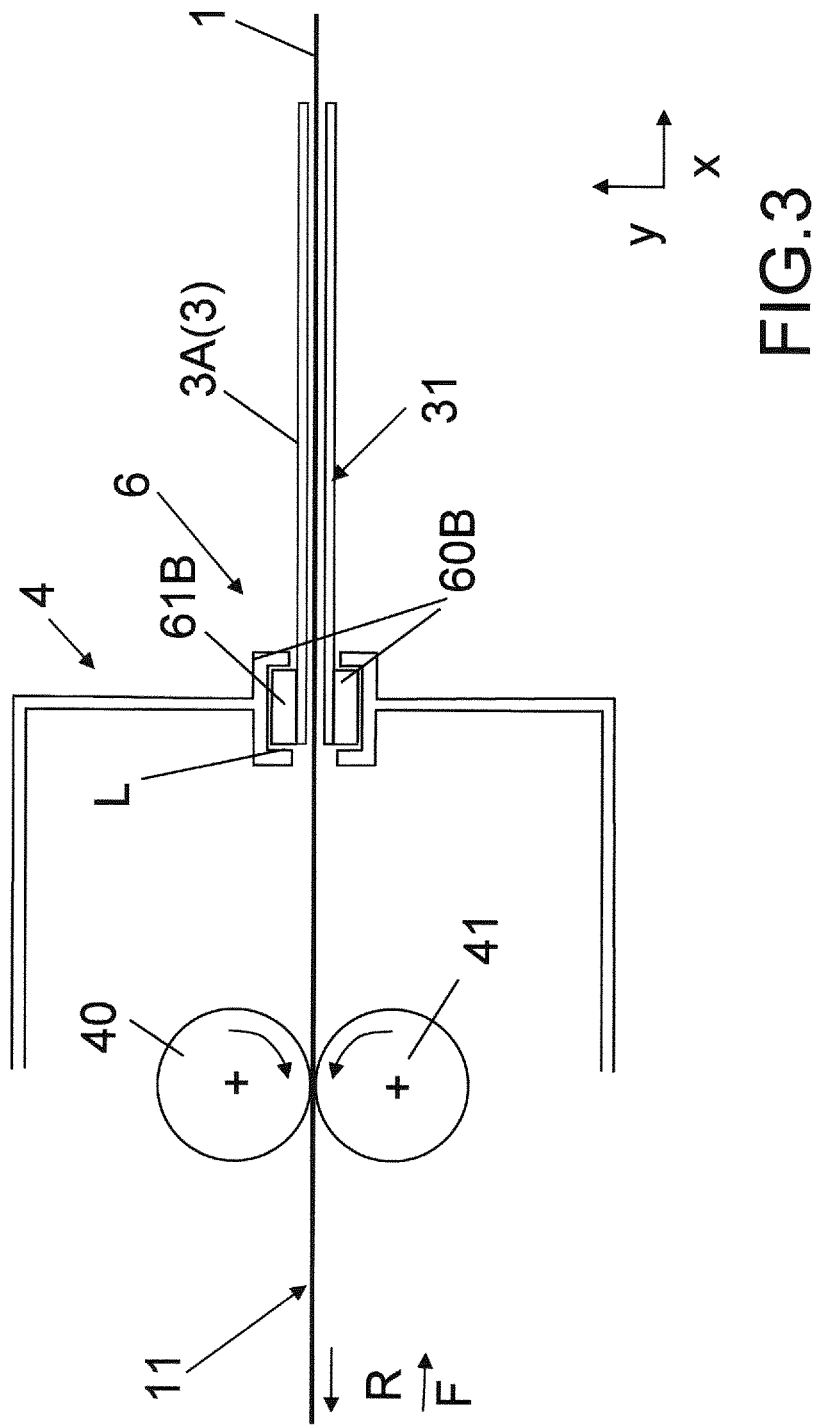
FIG. 3 is a cross-sectional view of a second embodiment of a connector for the proximal portion of the guide sheath of the device shown in FIG. 1.

FIGS. 2 and 3 show two different embodiments of a locking system 6.

In FIG. 2, the locking system 6 is a two-part connector 60A, 61A. The part 60A is a rigid male end terminal, which is provided on the retraction system 4, and which is attached with respect to the point of contact P of the optical fiber 1 between the two drive rollers 40, 41. This male end 60A has a thread 62A. The portion 61A is a rigid female connector, which is attached, for example by gluing, to the proximal end portion 31 of the sheath 3A. This 61A female connector has a thread 63A for screwing on the male end 60A.

In this exemplary embodiment, when the female connector 61A is screwed onto the male end part 60A, the proximal end portion 31 of the sheath is immobilized in all directions with respect to the removal system 4.

In FIG. 3, the locking system 6 is a two-part connector 60B, 61B. The part 60B is a rigid female end part, which is provided on the retraction system 4, and which is attached with respect to the point of contact P of the optical fiber 1 between the two drive rollers 40, 41. This female end 60B forms a housing L. The other part 61B of the connector is a male end which is attached, for example by gluing, to the proximal end portion 31 of the sheath 3A, and which can be inserted into housing L by translation along an axis perpendicular to the plane (X, Y) of FIG. 3.

In this embodiment of FIG. 3, when the male end 61B is positioned in the housing L of the female end 60B, the proximal end portion 31 of the sheath is immobilized relative to the retraction system 4 in all directions in the plane (X, Y) perpendicular to the axes of rotation A of the drive rollers 40, 41.

More generally, the locking system 6 must be designed so as to axially lock the proximal end portion 31 of the guide sheath 3A, with respect to the optical fiber 1, at least in the direction of retraction R of the optical fiber 1, and preferably also in the direction opposite to direction F of the optical fiber 1.

Figure 4:
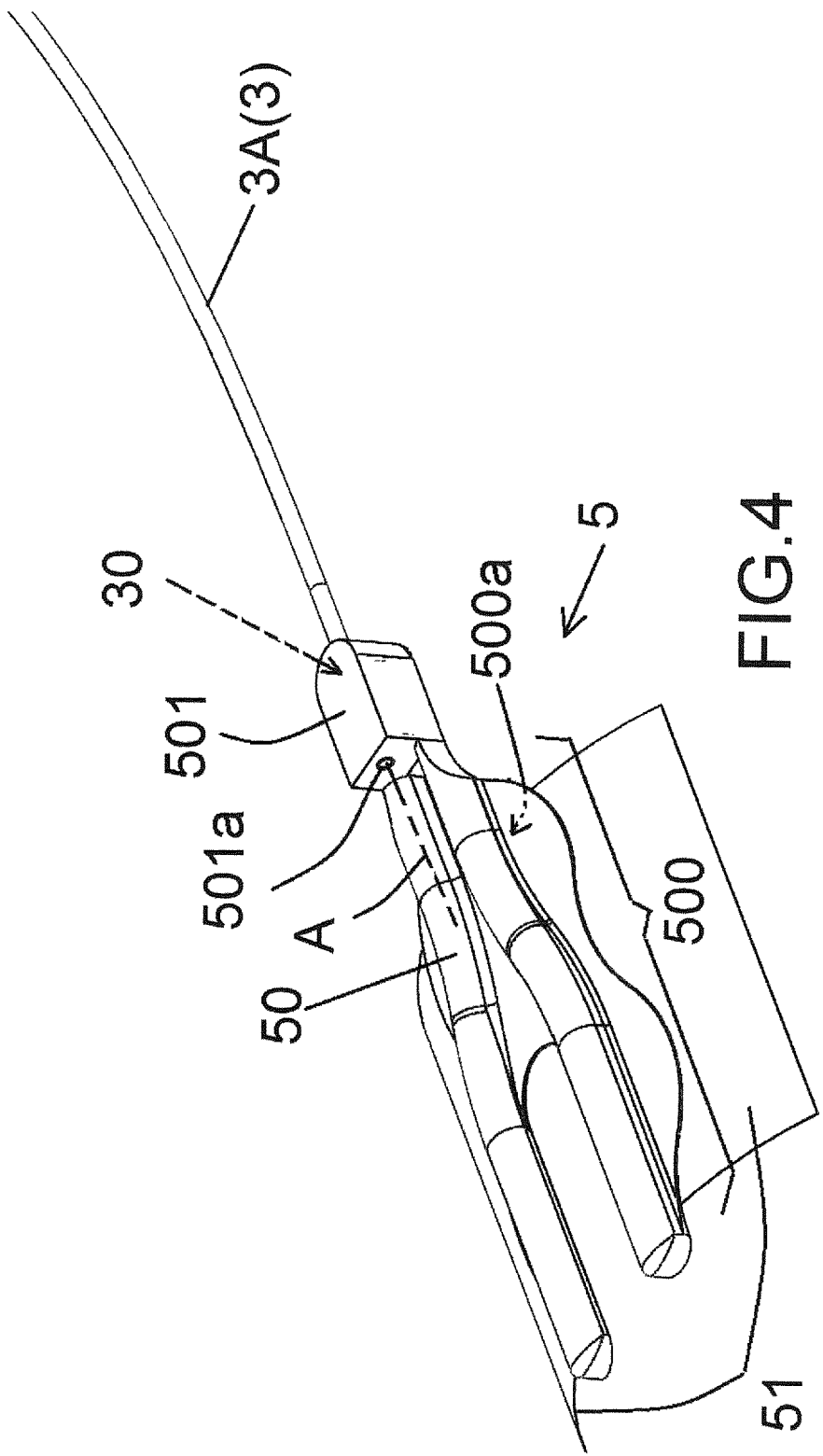
FIG. 4 is an isometric view of a first embodiment of a system for holding the distal portion of the guide sheath of the endovenous treatment device.
Figure 5:
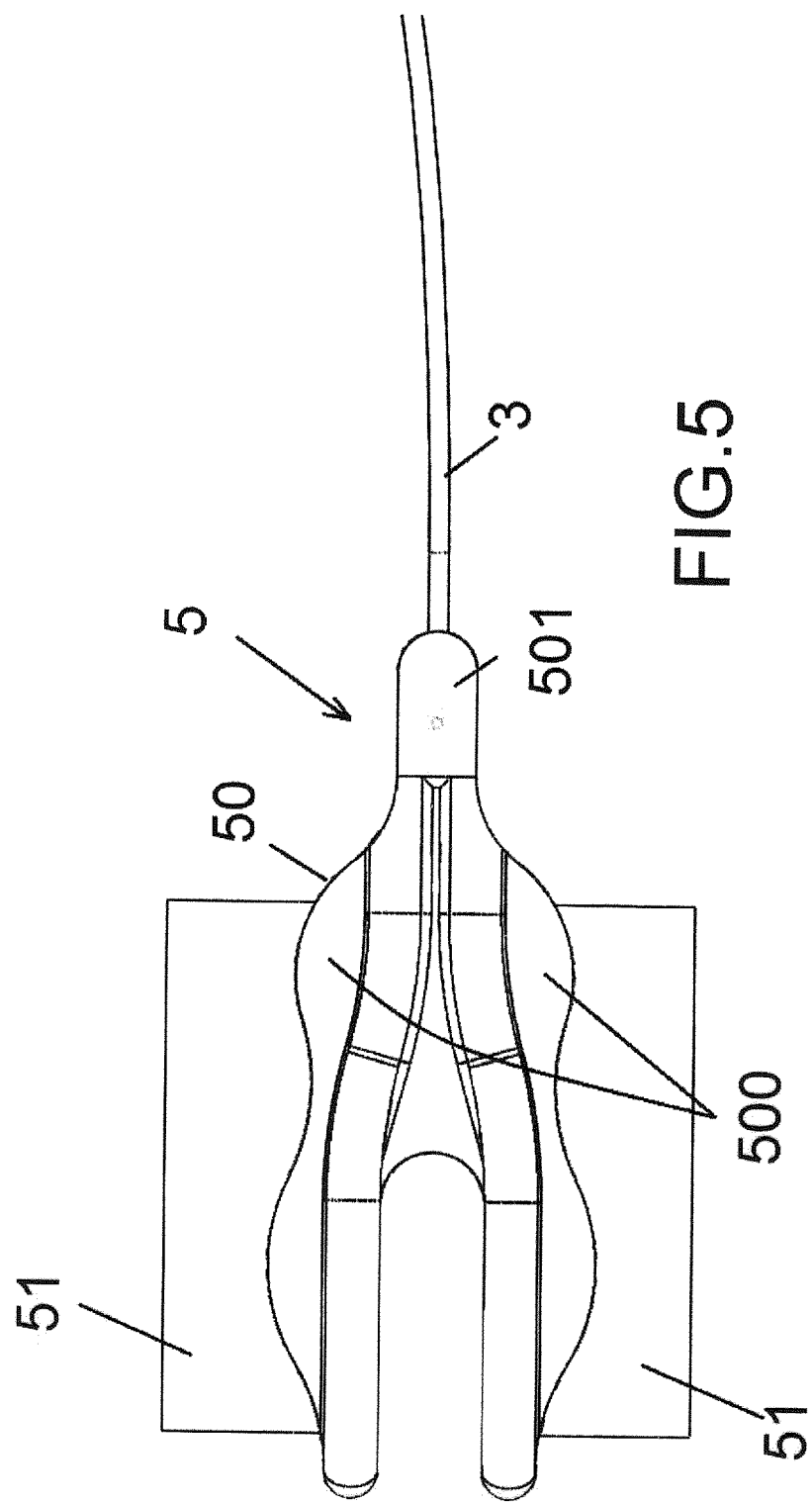
FIG. 5 is a view from above of the holding system of FIG. 4.
Figure 6:
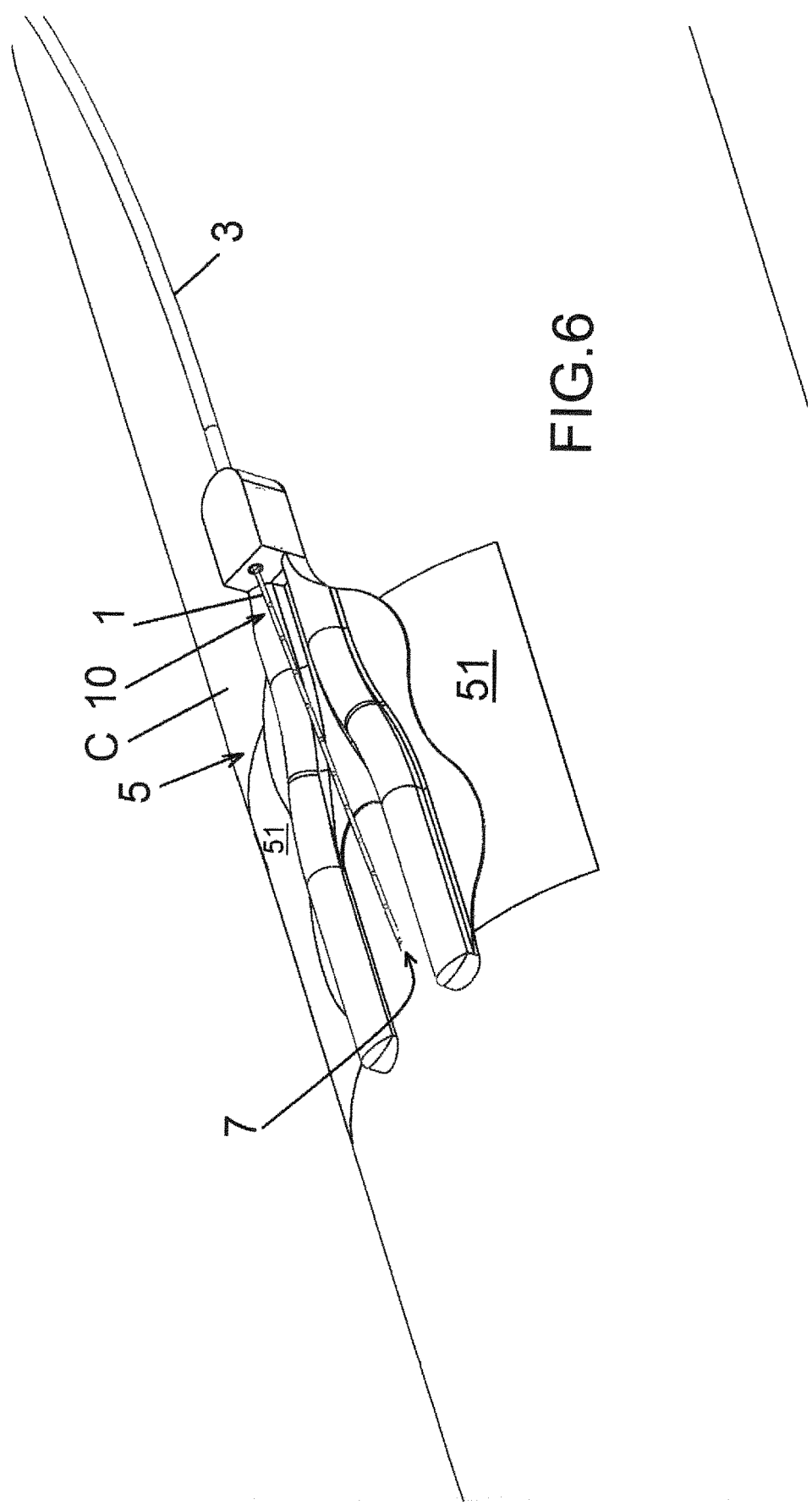
FIG. 6 is an isometric view of the holding system of FIG. 4 placed on and attached to a part of a human body, with the optical fiber inserted through the skin.
Figure 7:
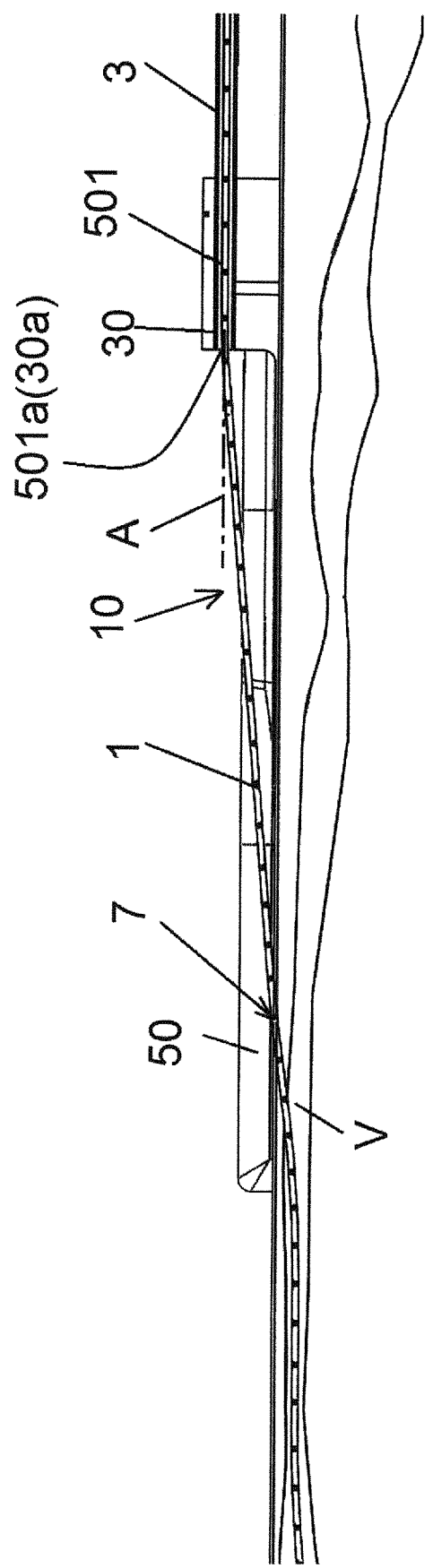
FIG. 7 is a longitudinal sectional view of FIG. 6, showing in particular the vein and the optical fiber inserted into the vein.

FIGS. 4 and 5 show a particular embodiment of a holding system 5 according to a first particular embodiment of the invention.

This holding system 5 comprises a holding part 50, which may be for example a plastic molded part. This holding part 50 comprises a main spatula-shaped front portion 500, the lower face 500a forms a support surface which is substantially flat or slightly curved and is intended to be applied against the human body. This main front portion 500 may be rigid or slightly flexible so as to adapt the curvature of its underside 500a to the human body part C.

This holding part 50 also has a connector 501 in the rear part, which enables the distal end portion 30 of the sheath 3A to be attached to the holding part 50. In the particular variant illustrated, this connector 501 comprises a tubular through passage 501a of longitudinal central axis A in which is slid and is attached, for example by gluing, the distal end portion 30 of the sheath 3A.

The longitudinal central axis A of the distal portion 30 of the guide sheath 3A which merges with the longitudinal central axis of the through passage 501a forms a guide axis of the optical fiber 1 which does not intersect the support surface formed by the lower face 500a of the holding part 50. The optical fiber 1 is thus able to slide in the direction of its length relative to the holding part 50 and the guide sheath 3A, being guided by the distal portion 30 of the guide sheath 3A along this guiding axis A.

This orientation of the guide axis A of the distal portion 30 of the guide sheath 3A, relative to the support surface formed by the lower face 500a of the holding part 50, thus allows the longitudinal insertion in a vein V of the proximal portion 10 of the optical fiber 1, over at least a part of its length, when the proximal end portion 30 of the guide sheath 3A is held relative to the body of a patient by means of the holding part 50.

More particularly, but in a non-limitative manner, in this example the guide axis A is substantially parallel to the support surface formed by the lower face 500a of the holding part 50.

The holding system 5 also comprises a fastening mean 51 which allows the holding part 50 to be temporarily attached to the body C, and thereby the distal end portion 30 of the guide sheath 3A, for the duration of endovenous treatment. In the particular embodiment illustrated, this attachment facility is a double-sided adhesive 51 which is pressed against the lower face 500a of the holding part 50 and which is designed to adhere in a removable manner to the skin.

This double-sided tape 51 may be replaced by any equivalent facility to temporarily attach the distal end portion 30 of the guide sheath 3A to the body C for the duration of endovenous treatment. This double-sided adhesive 51 may for example be replaced by an elastic or Velcro® strap or other, which is capable of surrounding the human body part at which the part of the vein to be treated is located and which allows the holding part 50 applied against this part of the human body to be held temporarily.

A particular example of implementation of the endovenous treatment device will now be detailed, with reference to FIGS. 4 to 7.

(a) The optical fiber 1 is manually slid into the guide sheath 3A until the distal end portion 10 of the optical fiber 1 exits through the distal end opening 30a of the guide sheath 3A and is positioned outside the guide sheath 3A and the through passage 501a of the holding part 50.

(b) The proximal end portion 11 of the optical fiber 1 is positioned in the retraction system 4 and the proximal end portion 31 of the sheath 3A is locked relative to the retraction system 4 using the locking system 6 previously described. Then, the proximal end 1a of the optical fiber 1 is coupled to the output of the electromagnetic radiation source 2

(c) The distal end portion 30 of the sheath is attached relative to the body C, by fixing the holding part 50 to the human body C near the insertion point 7 of the optical fiber 1.

(d) The part e of a hollow needle, commonly known as a puncture needle, is pressed down in the usual manner, through the skin and into the vein V to be treated, the distal tip being ultrasonically localized by means of an ultrasound probe. The insertion point of this needle corresponds to the insertion point 7 referred to above.

(e) A guidewire is inserted into this hollow needle and into the vein to be treated, and then the needle is removed.

(f) An introducer catheter 8 is slid onto the guidewire up to the entrance of the vein V and the guidewire is removed.

Figure 8:
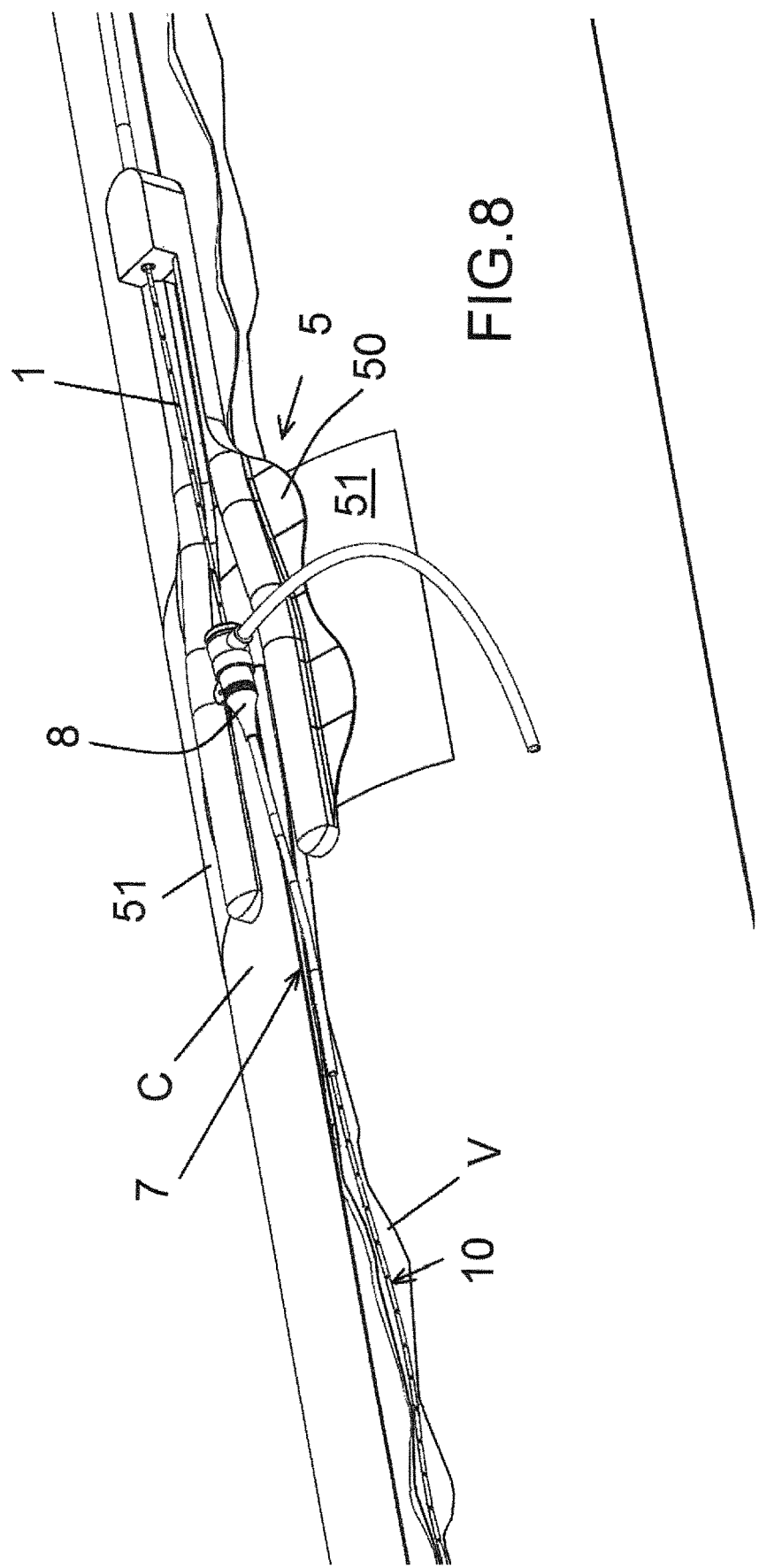
FIG. 8 is an isometric view illustrating a stage in the insertion of the distal end portion of the optical fiber into a vein, by means of an introducer catheter.

(g) Once the introducer catheter 8 has been inserted (FIG. 8), the distal end portion 10 of the optical fiber 1, which protrudes outside the distal end portion 30 of the sheath 3A, is inserted into the introducer catheter 8 and the optical fiber 1 is slid forwardly relative to the sheath 3A until the end of the distal end portion 10 of optical fiber 1 penetrates longitudinally into the vein V and progresses into vein V to the area to be treated furthest from insertion point 7. During this operation, the drive motor of the roller 40 is disengaged.

Figure 9:
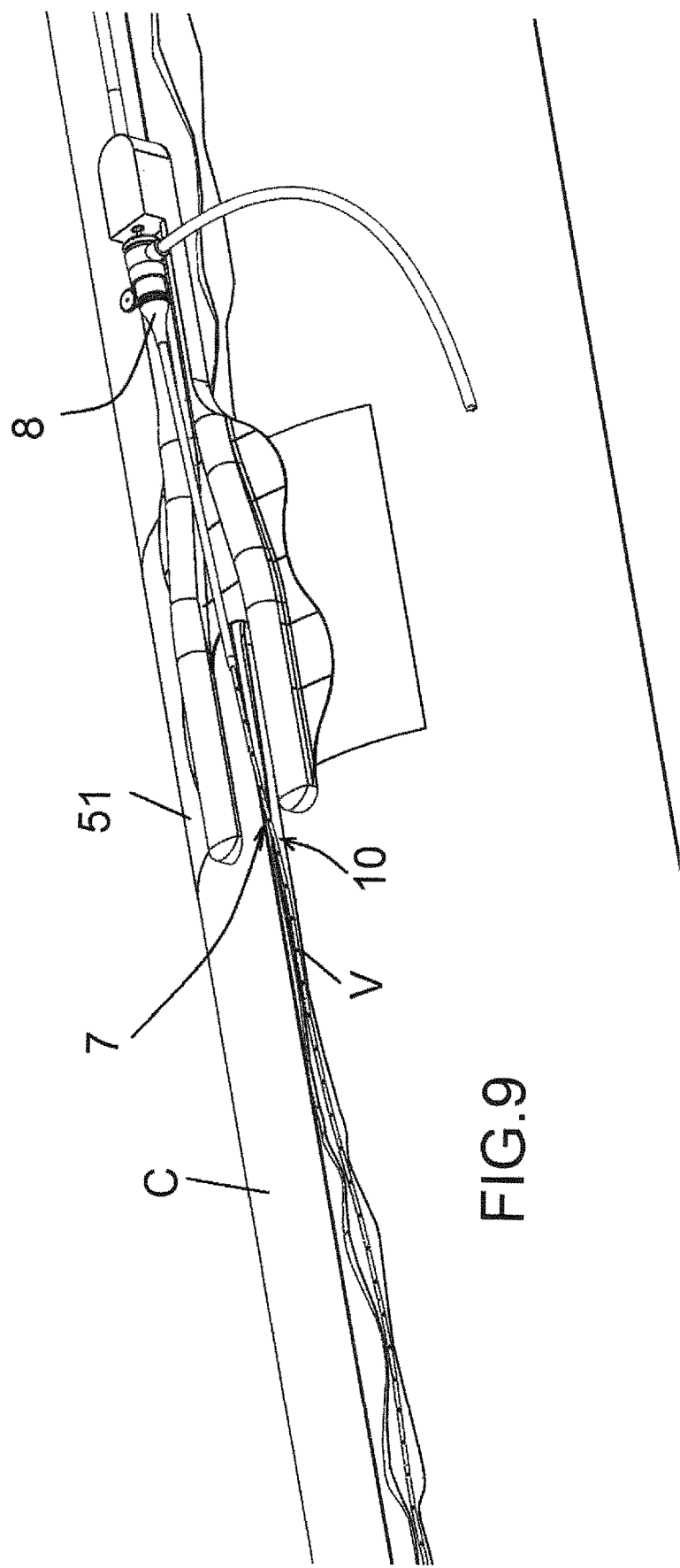
FIG. 9 is an isometric view showing the introducer catheter of FIG. 8 removed from the vein once the distal end portion of the optical fiber has been introduced into a vein.

(h) Once the optical fiber 1 is introduced and positioned into the vein V, the catheter 8 is withdrawn from the vein V by sliding it backwards along the optical fiber 1 (FIG. 9). Optionally, the catheter 8 is removed from the optical fiber 1, for example by splitting it in two in the case of a tearable catheter. In another variant, the catheter may be removed following completion of the treatment procedure.

The practitioner may then conduct the endovenous treatment as normal by manually operating the laser source 2, in order to emit electromagnetic radiation into the vein in the region of the end of the distal portion of the optical fiber 1 and by controlling the retraction, whether continuous or step by step, of the optical fiber 1 by means of the retraction system 4.

Thanks to the guide sheath 3A, whose distal end portion 30 is temporarily attached to the body C, near the insertion point 7 of the optical fiber 1, and whose proximal end portion 31 is locked axially relative to the optical fiber 1 by means of the locking system 6, the endovenous treatment can advantageously be performed without the optical fiber 1 being tensioned and reducing the risk of accidental movement of the optical fiber relative to the vein being treated.

Once the laser treatment is complete, the optical fiber 1 is completely removed from the vein and the holding system 5 is separated from the human body.

The removal system 4 can in a more general manner be replaced by any drive system allowing the treatment dose delivery wired element 1 to be drawn in at least one given drive direction R. This drive system 4 of the device is not necessarily motorized, but could be a manually operated drive system.

In the context of the invention, the guide sheath 3A can be replaced by any equivalent flexible guide that fulfills the same guiding function as the sheath 3A. For example, and non-exhaustively, the sheath 3A may be replaced by a flexible groove-shaped guide, having for example a U-shaped cross section, or by a flexible guidewire twisted around the optical fiber 1 or equivalent, or by a flexible guide which is magnetized to allow it to be secured to the wired element 1 for delivery of the treatment doses.

The holding system 5 may comprise only the holding part 50 or equivalent and may not include the fastening means 51 or equivalent. In this case, the holding part 50 is used to temporarily hold the distal end portion 30 of the guide 3 manually relative to the patient's body near the insertion point 7 of the wired treatment dose delivery element 1.

The holding system may comprise an attachment facility for temporarily attaching the distal end portion 30 of the guide 3 on the body of a patient, near the insertion zone 7 of the wired treatment dose delivery element 1, without use of the holding part 50. For example, the holding system may be formed of one or more adhesives capable of being applied directly to the distal end portion 30 of the guide 3 and to be adhered to the patient's body to temporarily attach the distal end portion 30 of the guide 3 relative to the body of the patient near the insertion point 7 of the wired treatment dose delivery element 1.

Figure 10:
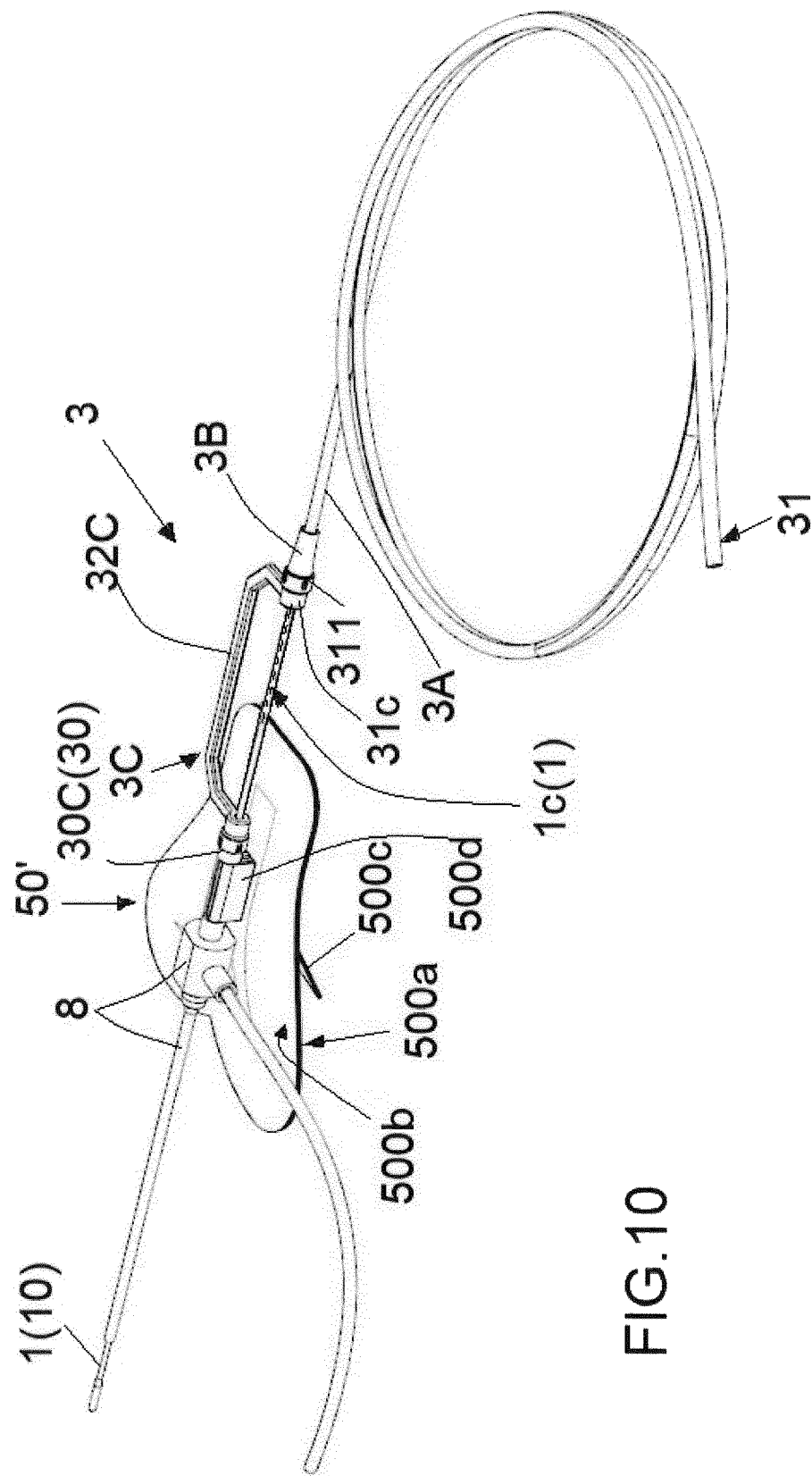
FIG. 10 is an isometric view of a second variant of a system for holding the distal end portion of the guide of the endovenous treatment device.
Figure 11:
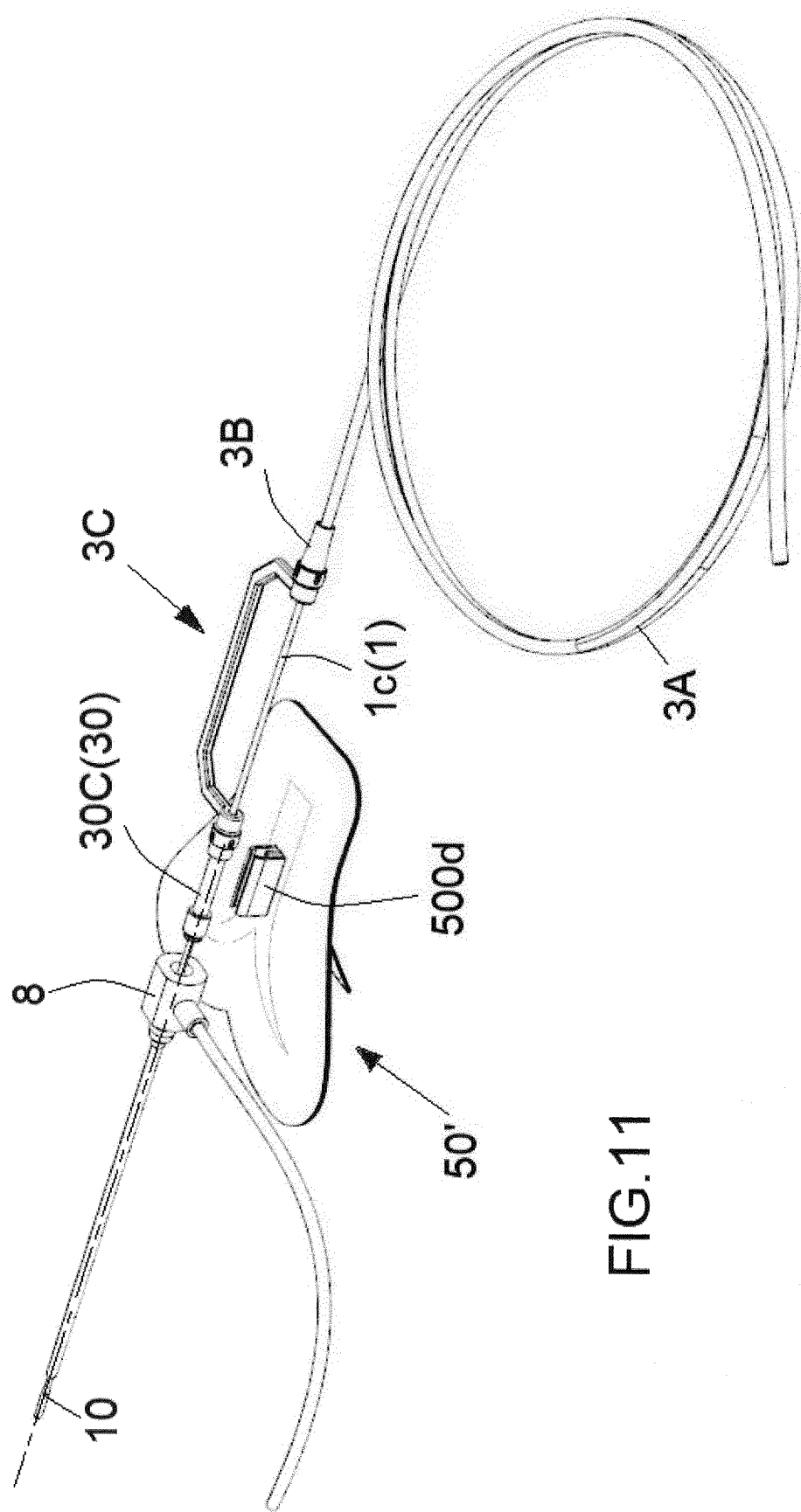
FIG. 11 is an isometric view of the holding system of FIG. 10, when the guide is not assembled with the holding part.

On FIGS. 10 to 13 is shown a second embodiment of the invention in which the guide 3 comprises multiple assembled guide elements, and the holding system 5 comprises a holding part 50' (FIG. 13) which is designed to be removably attachable with the guide 3 (FIGS. 10 and 11).

Figure 12:
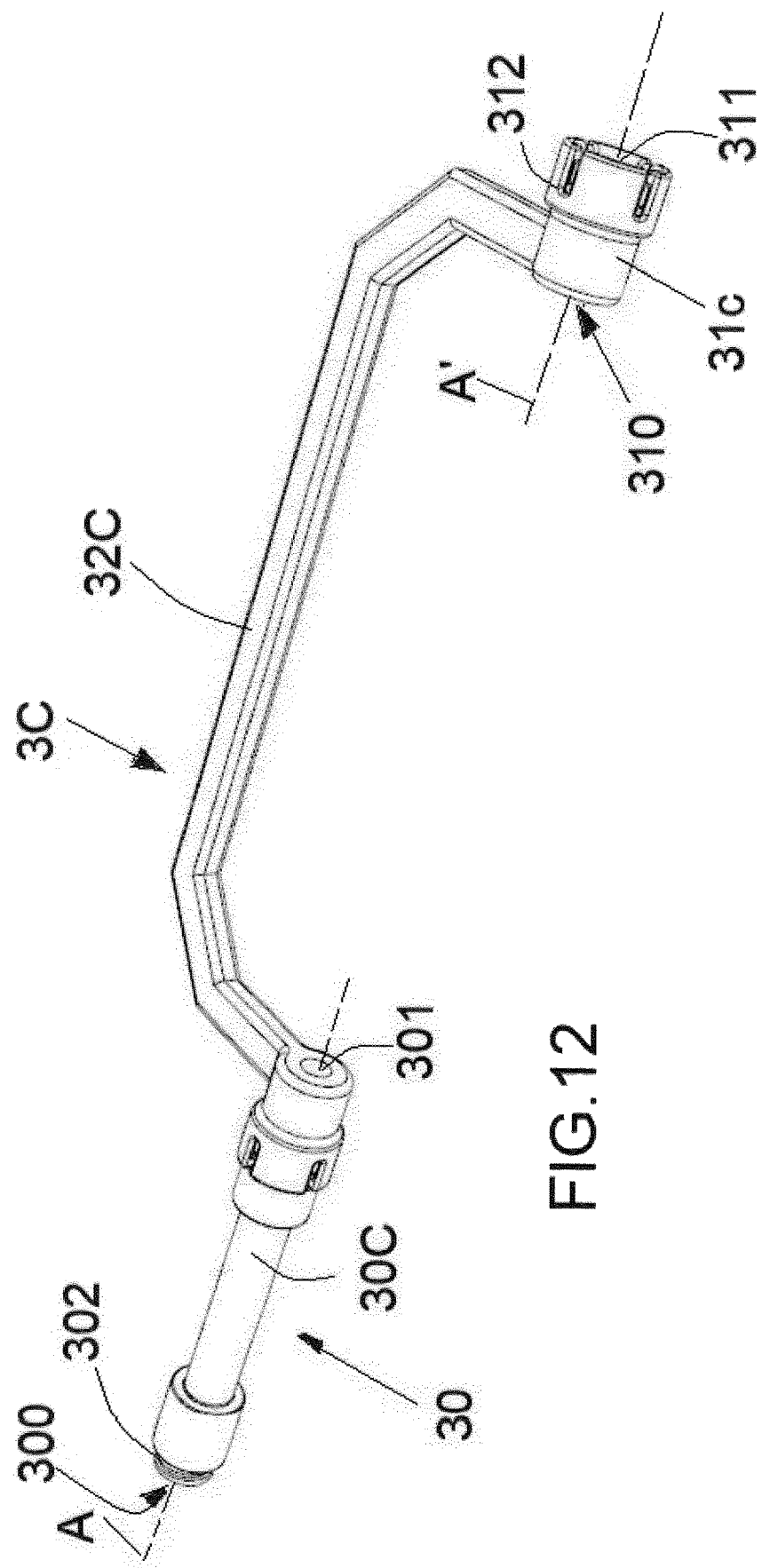
FIG. 12 is an isometric view of a guide part of the guide of the endovenous treatment device shown in FIG. 10.

The guide 3 comprises a flexible guide sheath 3A fitted to one end of a connector 3B and rigid guide part 3C, which is shown alone in FIG. 12 and which is rigidly attached (FIG. 10) to the proximal end of the flexible sheath 3A by means of the connector 3B.

In this embodiment, as for the first variant described above, the proximal end portion 31 of the guide sheath 3A can be locked axially with respect to the optical fiber 1 by means of a locking system 6, described above and not shown in FIGS. 10 to 13.

The guide part 3C may be for example a plastic part. This guide part 3C includes:
a tubular guide member 30C, which forms said distal end portion 30 of the guide 3, and which defines a guide axis A (FIG. 12) of the optical fiber 1, a front opening 300 and a rear opening 301 for the passage of the optical fiber 1,
a tubular rear guide member 31C, which defines a guide axis A' (FIG. 12) aligned with the guide axis A, a front opening 310 and a rear opening 311 for the passage of the optical fiber 1,
a rigid U-shaped connecting member 32C connecting the front tubular guide member 30C to the rear guide tubular member 31C remotely with respect to the aligned guide axis A and A'.

The tubular rear guide member 31C further comprises a connector 312 designed to interoperate, and in particular to be fitted with clamping, with the connector 3B attached to the end of the guide sheath 3A.

The front guide tubular element 30C comprises an assembly facility 302 (FIG. 12), in this case in the form of a thread, for its temporary assembly, in particular by screwing, with an introducer catheter 8 (FIG. 10).

Referring to FIGS. 10 and 11, the guide part 3C is joined to the distal end of the guide sheath 3A by means of the connectors 311 and 3B, by being slid onto the optical fiber 1. The optical fiber 1 can slide in the direction of its length with respect to the guide sheath 3A and with respect to the guide part 3C, while being guided outside the guide sheath 3A by the two tubular guide elements 30C and 31C.

Figure 13:
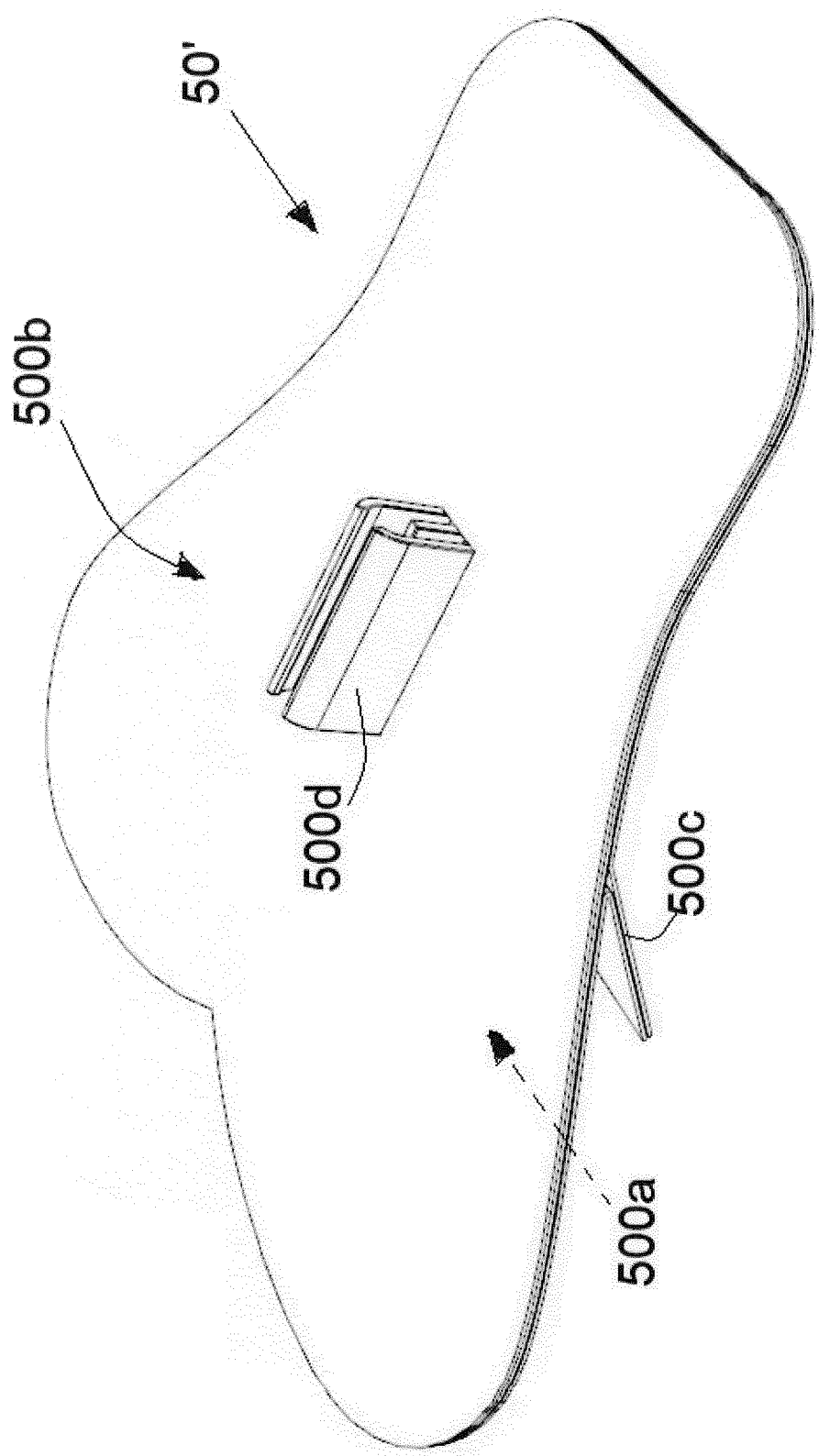
FIG. 13 is an isometric view of the holding part of the holding system shown in FIG. 10.

Referring to FIG. 13, the holding part 50' is a part of small thickness, for example a molded plastic part, whose lower face 500a forms a substantially flat or slightly curved support surface and is intended to be applied against the human body. This holding part 50 may be rigid or slightly flexible so as to adapt the curvature of its lower face 500a to the human body part C.

The bottom face 500a of the holding part 50' may be coated with an adhesive layer covering all or part of its surface and temporarily protected with a protective film 500c which may be removed manually before use. This adhesive layer forms an attachment facility for temporarily fixing the holding part 50' applied to the body of a patient near the insertion point 7 of the optical fiber 1.

This holding part 50' also has on its upper face 500b, an assembly facility 500d, for example in the form of an elastically deformable clip, which allows quick assembly of the holding part 50' with the tubular element of front guide 30C of the guide part 3C of the guide 3, that is to say with the distal end portion 30 of the guide 3.

Referring to FIG. 10, the holding part 50' is designed to be assembled with the distal end portion 30 (tubular front guide element 30C) of the guide 3, so that the guide axis A (FIG. 12) of the distal end portion 30 of the guide 3, does not intersect the support surface formed by the lower face 500a of the holding part 50'. The optical fiber 1 is thus able to slide in the direction of its length relative to the holding part 50' and to the guide 3, being guided by the distal portion 30 of the guide 3 along this guide axis A which does not intersect the support surface formed by the lower face 500a of the holding part 50'.

This orientation of the guide axis A of the distal portion 30 (tubular front guide element 30C) of the guide 3 relative to the support surface formed by the lower face 500a of the holding part 50', thus allows longitudinal insertion into a vein V of the distal portion 10 of the optical fiber 1, over at least a part of its length, when the distal end portion 30 of the guide 3 is held relative to the body of a patient by means of the holding part 50'.

More particularly, but in a non-limitative manner, in this example the guide axis A does not intersect the support surface formed by the lower side 500a, and more particularly is substantially parallel to said support surface which is flat or substantially flat.

In the variant described in FIGS. 10 to 13, the optical fiber 1 is preferably accessible to an operator along its portion 1c (FIG. 10) located between the frontal tubular guide element 30C and the rear tubular guide element 31C, which advantageously allows an operator to manipulate the optical fiber 1 by hand, if necessary to make adjustments to its position in a vein V, by pulling locally on the optical fiber 1 to the rear or by pushing locally the optical fiber 1 forward towards the vein.

A particular example of implementation of the endovenous treatment device of FIG. 10 will now be detailed, the introducer catheter 8 is not attached to the proximal end portion 30 of the guide 3, and the distal end portion 10 of the optical fiber 1 protruding from the distal end portion 30 of the guide 3.

(a) the proximal end portion 11 of the optical fiber 1 is positioned in the retraction system 4 and the proximal end portion 31 of the sheath 3A is locked relative to the retraction system 4 using the locking system 6 previously described. Then the proximal end 1a of the optical fiber 1 is coupled to the output of the electromagnetic radiation source 2.

(b) The distal end portion 30 of the guide 3 is attached relative to the body C, by attaching the holding part 50' to the human body C near the insertion point 7 of the optical fiber 1.

(c) The distal portion of a hollow needle, commonly known as a puncture needle, whose tip is ultrasonically localized by means of an ultrasound probe, is routinely pushed through the skin and into the vein V to be treated. The insertion point of this needle corresponds to the insertion point 7 referred to above.

(d) A guidewire is inserted into this hollow needle into the vein to be treated, and then the needle is removed.

(e) The introducer catheter 8 is slid onto the guidewire to the inlet of the vein V and the guidewire is removed.

(f) Once the introducer catheter 8 has been inserted, the distal end portion 10 of the optical fiber 1, which protrudes outside the distal end portion 30 of the guide 3, is inserted into the introducer catheter 8 and the optical fiber 1 is slid forward relative to the sheath 3A, until the end of the distal end portion 10 of optical fiber 1 penetrates longitudinally into the vein V and progresses in the vein V up to the area to be treated furthest from insertion point 7. During this operation, the drive motor of the roller 40 is disengaged.

(g) Once the optical fiber 1 is introduced and positioned in the vein V, the catheter 8 is slid backwards onto the optical fiber 1 and attached to the distal end 30 of the guide 3 as illustrated in FIG. 10. The catheter 8 will be removed following completion of the treatment procedure.

Step (g) is optional. Step (b) may be performed after step (f).

The practitioner can then routinely conduct the endovenous treatment by manually operating the laser source 2, in order to emit electromagnetic radiation into the vein in the region of the end of the distal portion of the optical fiber 1 and by controlling the retraction, whether continuous or step by step, of the optical fiber 1 by means of the retraction system 4.

Figure 14:
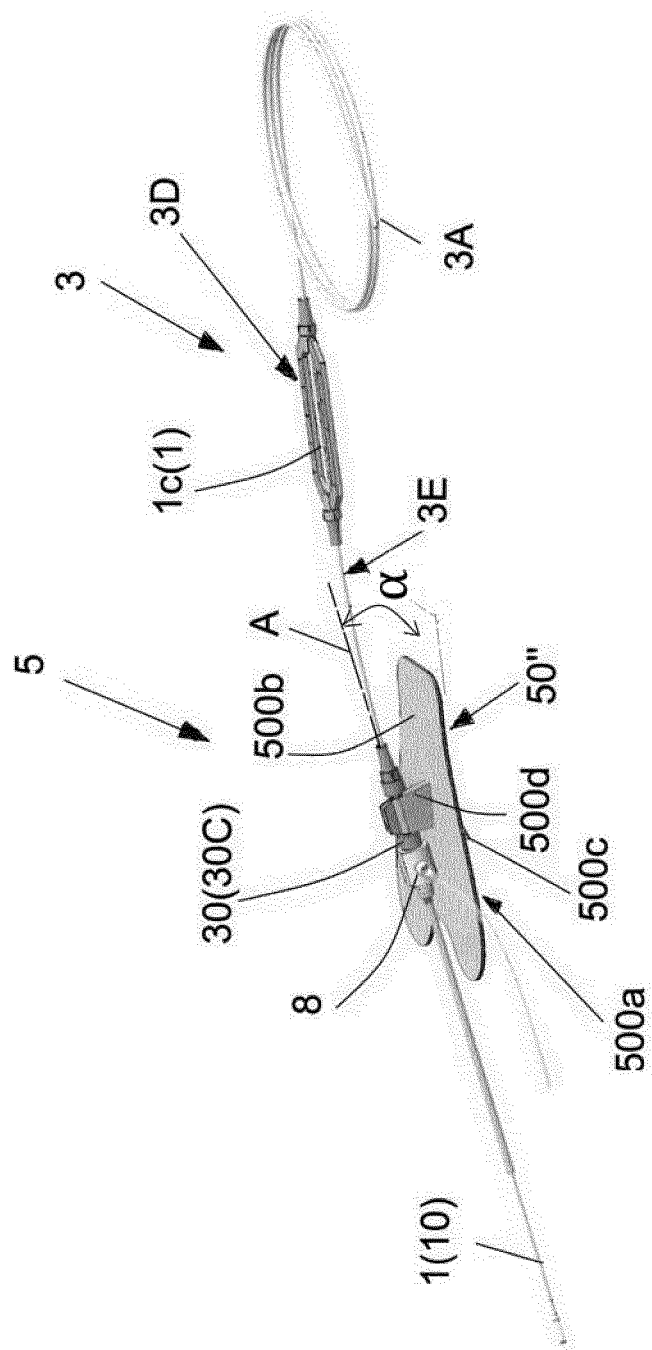
FIG. 14 is an isometric view of a third variant of a system for holding the distal end portion of the guide of an endovenous treatment device.

A third variant of the invention is shown in FIG. 14.

In this variant the support surface which is formed by the lower face 500a of the holding part 50" is flat or substantially flat, and the distal end portion 30 of the guide 3 formed by the tubular front guide element 30C is assembled with the holding part 50" by means of the assembly clip 500d, so that, as for the second variant referred to above, the guide axis A of this distal end portion 30 of the guide 3 does not intersect this support surface.

Unlike the second variant referred to above, this guide axis A is not substantially parallel to the support surface which is formed by the lower face 500a of the holding part 50', but is inclined with respect to this support surface 500a by an angle $\alpha$ which allows the longitudinal insertion of the optical fiber in a vein, by sliding forward of the optical fiber 1 in the direction of its length, when the support surface 500a is applied against the body of a patient.

Preferably, this angle $\alpha$ is less than or equal to 60° and more preferably is less than or equal to 45°, and more preferably is less than or equal to 30°. This inclination of the guide axis A facilitates the introduction of the optical fiber 1 into a vein in comparison to the second variant described above.

In another variant (not shown), the guide axis A may traverse the support surface which is formed by the lower face 500a of the holding part 50". In this case, the lower face 500a of the holding part 50" which defines a support surface which is flat or substantially flat, the guide axis is inclined relative to the support surface 500a by an angle $\alpha$ which allows the longitudinal insertion of the optical fiber into a vein, by sliding the optical fiber forward in the direction of its length, when the support surface 500a is applied against the body of a patient. Preferably this angle $\alpha$ is less than or equal to 60°, preferably less than or equal to 45° more preferably less than or equal to 30°.

It should be noted that within the framework of the invention, the lower face 500a of the holding part 50, 50' or 50" may be rigid and define a support surface on the body which is flat or substantially flat or may be deformable when it is pressed against the body and may define, in its deformed state, when pressed against the body, a support surface on the body which is flat or substantially flat.

In this third embodiment, the flexible guide sheath 3A is connected to the tubular front guide element 30C (forming the proximal end portion of the guide 3) by a rigid guide part 3D, made for example of plastic, slid onto the optical fiber 1 and attached to the proximal end of the sheath 3A, and a flexible sheath 3E of short length, slid onto the optical fiber 1 and attached to the proximal end of the connecting part 3D and to the proximal end of the tubular front guide element 30C. The flexibility of this sheath 3E enables the forces transmitted to the distal end portion 30 of the guide 3 to be limited during manipulation of the endovenous device.

The 3D connecting part is designed such that a portion 1c of the optical fiber 1 is bare and is thus advantageously accessible for an operator (FIG. 14), which advantageously allows an operator to manipulate the optical fiber 1 by hand if necessary to make adjustments to its position in a vein V, by pulling this portion 1c of the optical fiber backwards or by pushing this portion 1c of the optical fiber 1 to the front in the direction of the vein.

In the variant described in the accompanying figures, the lower face 500a of the holding part 50, 50', 50" forms a continued support surface. In another variant, this support surface may be discontinuous and defined by spaced support members.

The invention is not limited to an endovenous laser treatment device. In other variations covered by the invention, the optical fiber may be replaced by a wired element (solid or hollow) for example of the cable or flexible probe or flexible cannula type. The treatment may not necessarily be a laser treatment, but may be any treatment consisting of the delivery of doses of treatment into the vein, and especially of doses of energy, delivered for example in the form of electromagnetic radiation, by means of sound or ultrasonic waves, radiofrequency waves, or doses of thermal energy delivered by radiation and/or by contact, or doses of a product, for example liquid, semi-liquid or foam, allowing treatment of the vein.

The invention claimed is:

1. An endovenous treatment device having a delivery system of at least one treatment dose, the delivery system comprises a wired treatment dose delivery element which is flexible, which has a distal end portion capable of being inserted, at least over part of its length, longitudinally into a vein, and which is adapted for delivery into the vein of at least one treatment dose in a region of the end of said distal end portion, the endovenous treatment device further comprising a drive system for driving of the wired treatment dose delivery element in at least a given first drive direction, a guide which is flexible over all or part of its length, which has a proximal end portion and a distal end portion, and which allows the wired treatment dose delivery element to be guided over a portion of its length with a proximal end portion and, at the opposite end, a distal end portion of the wired treatment dose delivery element, which are not guided by the guide, a holding system which is positioned at the distal end portion of the guide and enables the distal end portion of the guide to be temporarily held relative to the body of a patient, near an insertion zone of the wired treatment dose delivery element, and a lock which allows the proximal end portion of the guide to be locked axially relative to the drive system, at least in the first drive direction of the wired treatment dose delivery element, the wired treatment dose delivery element being slidable in the direction of its length relative to the guide, so as to allow insertion longitudinally into the vein of the distal end portion of the wired treatment dose delivery element over at least a portion of its length.

2. The device according to claim 1, wherein the holding system comprises a holding part which is designed to be applied to the body of a patient so as to temporarily maintain the distal end portion of the guide relative to the body of a patient, near the insertion zone of the wired treatment dose delivery element.

3. The device according to claim 2, wherein the holding part has an underside for applying the holding part in contact with the body of a patient, and wherein the wired treatment dose delivery element is slidable along the direction of its length, guided by the distal end portion of the guide along a guide axis which does not intersect the lower face of the holding part.

4. The device according to claim 3, wherein the underside of the holding part forms a support surface, and wherein the wired treatment dose delivery element is slidable in the direction of its length being guided by the proximal portion of the guide, along said guide axis which does not intersect the support surface.

5. The device according to claim 4, wherein the underside of the holding part forms a support surface which is flat, or is capable of being deformed so as to form a support surface which is flat when applied to a body, and the guide axis is parallel to this support surface of the holding part.

6. The device according to claim 4, wherein the guide axis is inclined relative to the support surface of the holding part at an angle ($\alpha$), which allows the insertion longitudinally of the wired vein treatment dose delivery element, by sliding the wired element for delivery treatment dose in the direction of its length, when the support surface is applied against the body.

7. The device according to claim 2, wherein the holding part has a lower face for applying the holding part in contact with the body of a patient, wherein the lower face of the holding part forms a support surface which is flat, or is capable of being deformed so as to form a support surface which is flat when it is applied to a body, in which the wired treatment dose delivery element is capable of sliding in the direction of its length, being guided by the distal end portion of the guide along a guide axis, which passes through this support surface and which is inclined with respect to this support surface by an angle ($\alpha$) permitting longitudinal insertion of the wired treatment dose delivery element into the vein, by sliding of the wired treatment dose delivery element in the direction of its length, when the support surface is applied against the body.

8. The device according to claim 6, wherein said angle ($\alpha$) is less than or equal to 60°.

9. The device according to claim 2, wherein the holding part is permanently attached or is adapted to be permanently or removably attached to the distal end portion of the guide.

10. The device according to claim 2, wherein the holding part comprises a tubular through passage in which is slid and is attached the distal end portion of the guide.

11. The device according to claim 1, further comprising an introducer catheter which is designed to be temporarily assembled with the distal end portion of the guide.

12. The device according to claim 1, wherein the guide is designed such that once the wired treatment dose delivery element is slid in the guide, there remains in the guide a portion of the wired treatment dose delivery element that is accessible and positioned to be manipulated by an operator.

13. The device according to claim 1, wherein the holding system comprises attachment facilities which temporarily attach the distal end portion of the guide, onto the body of a patient near the insertion area of the wired treatment dose delivery element.

14. The device according to claim 13, wherein the attachment facility comprises an adhesive or an adhesive layer capable of bonding to the skin.

15. The device according to claim 1, wherein the drive system is a retraction system which drives the wired treatment dose delivery element rearward in the first drive direction allowing the removal from the vein of the distal end portion of the wired treatment dose delivery element.

16. The device according to claim 1, wherein the lock are also designed to axially lock the proximal end portion of the guide in the direction opposite to the first drive direction of the wired treatment dose delivery element.

17. The device according to claim 1, wherein the wired treatment dose delivery element is an optical fiber.

18. The device according to claim 17, comprising a source of electromagnetic radiation which is adapted to be coupled to the optical fiber.

19. The device according to claim 1, wherein the comprise a two-part connector, a fixed part which is attached on the drive system, and a removable part which is attached to the proximal end portion of the guide and is designed to interoperate with the fixed part for locking of the proximal end portion of the guide.

20. The device according to claim 1, wherein the guide comprises a flexible guide sheath.

21. The device according to claim 1, wherein the guide comprises several assembled guide elements, including at least one flexible guiding element.

22. A method of endovenous treatment with a wired treatment dose delivery element, which is flexible and is guided over a portion of its length by means of a guide, with a proximal end portion, and on the opposite side, a distal end portion of the wired treatment dose delivery element, which are not guided by the guide, said guide being flexible over all or part of its length, said method comprising at least the following operations:

(1) axial locking of a proximal end portion of the guide, relative to a drive system and in at least one drive direction of the wired treatment dose delivery element;

(2) temporary holding of a distal end portion of the guide outside a patient's body and relative to the patient's body;

(3) longitudinal insertion of the distal end portion of the wired treatment dose delivery element into a vein to be treated, at least over part of its length, the order of operations (1), (2) and (3) being of no significance;

(4) delivery of one or more treatment doses to the vein by means of the wired treatment dose delivery element and in a region of the distal end of the wired treatment dose delivery element,
(5) the distal end portion of the wired treatment dose delivery element is moved in the vein by driving the proximal end portion of the wired treatment dose delivery element in said at least one drive direction,
operations (4) and (5) are performed simultaneously or successively or repeatedly.

23. The method of claim 22, wherein the wired treatment dose delivery element is an optical fiber, and the step (4) further comprises the emission of electromagnetic radiation into the vein by means of this optical fiber.

24. The method of claim 22 wherein step (2) further comprises temporary attaching the distal end portion of the guide to the body of the patient.

25. The method of claim 23 wherein step (2) further comprises temporary attaching the distal end portion of the guide to the body of the patient.

\* \* \* \* \*